Figure 1A:
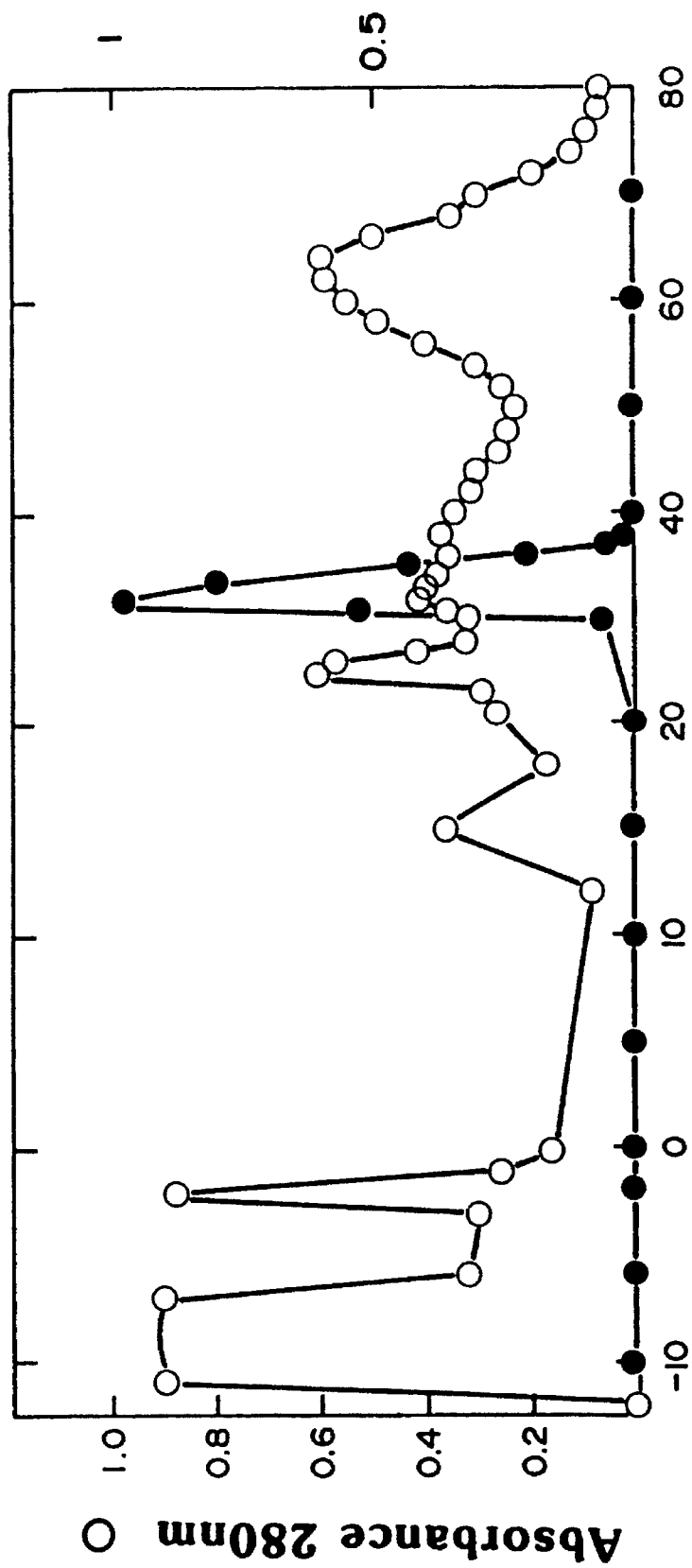

United States Patent [19]
Chelladurai et al.

[11] Patent Number: 5,529,934
[45] Date of Patent: Jun. 25, 1996

[54] METHOD FOR MEASURING BLOOD PROCOAGULANT ACTIVITY OF HUMAN LEUKOCYTE ANTIGENS

[75] Inventors: Mohanathasan Chelladurai, Southfield; Kenneth V. Honn, Grosse Pointe Woods; Daniel A. Walz, Detroit, all of Mich.

[73] Assignee: Biomide Investment Limited Partnership, Grosse Pointe Farms, Mich.

[21] Appl. No.: 737,441

[22] Filed: Jul. 29, 1991

[51] Int. Cl.$^6$ .......................... C12Q 1/00; A61K 39/085; C07K 1/00; A01N 37/18
[52] U.S. Cl. .................. 436/69; 435/4; 435/7.2; 424/243.1; 530/350; 514/2
[58] Field of Search .................. 424/92, 243.1; 514/2, 8; 530/300, 350, 395; 435/4, 7.2; 436/69

[56] References Cited

U.S. PATENT DOCUMENTS 4,478,823  10/1984  Sanderson ........................ 424/88

OTHER PUBLICATIONS

Kabawat, S. E. et al. (1983) Int. J. Cancer 32:547–554.
Parmiani, G. et al. (1985) Cancer Metastazois Rev. 4:7–26.
Zaleski, M. B. et al. *Immunogenetics*, Pittman Publishing Inc., MA, 1983, pp. 283, 325.
Helin, H. et al. (1983) J. Exp. Med. 158:962–975.
Herrmann, T. et al. (1989) Eur. J. Immunol. 19:2171–2174.
Janeway, C. A. et al. (1989) Immunol. Rev. 107:61–88.
Rickles, F. R., et al., Blood 62:14–31 (1983).
Weiss, L., et al., Clin. Expl. Metas. 7:127–167 (1989).
Honn, K. V., et al., Biochem. Pharm. 34:235–241 (1985).
Honn, K. V., et al., FASEB. J. 3:2285–2293 (1989).
Gorelik, E., Cancer Res. 47:809–815 (1987).
Broze, G. J., et al., J. Biol. Chem. 260:10917–10920 (1985).
Guha, A., et al., Proc. Natl. Acad. Sci. USA 83:299–302 (1986).
Gordon, S. G., et al., J. Clin. Invest. 67:1665–1671 (1981).
Cavanaugh, P. G., et al., Thromb. Res. 37:309–326 (1985).
Sakai, T., et al., J. Biol. Chem. 265:9105–9113 (1990).
Laemmli, U. K., 6th Floor Nature (London), 227:680–685 (1970).
Read, S. M., et al., Anal. Biochem. 116 53–64 (1981).
Lee, J. S., et al., Nature. 299:750–752 (1982).
Donati, M. B., et al., In: Recent Advances in Blood Coagulation (Ed. L. Poller), Churchill Livingstone, Edinburgh, pp. 227–259 (1982).
Chelladurai, M., et al., Proc. Am. Ass. Can. Res. 29:68a (1988) (abstract 270 considered).
Gorga, J., et al., J. Biol. Chem. 262:16087–16094 (1987).
Daar, A. S., et al., J. Immunol. 129:447–449 (1982).
Winchester, R. J., Proc. Natl. Acad. Sci. USA. 75:6235–6239 (1978).
Basham, T. Y., et al., J. Immunol. 130:1492–1494 (1983).
Rozhin, J., et al., Cancer Res. 47:6620–6628 (1987).

DeDuve, C., et al., Biochem J. 4th Floor 60:604–617 (1955).
Roitt, I., et al., Immunology pp. 4.1–4.12 (1986).
CRC Handbook Series in Clinical Lab. Science Section I Hematology, vol III:301 (1980).
Sandberg, H., et al. Throm. Res. 14:113–124 (1979).
Shapiro, S. S., et al., In Hemostasis and Thrombosis (eds. E. J. W. Bowie and A. A. Sharp), Butterworth, London, pp. 197–236 (1985).
Fleischer, B., et al., Cell. Immunol. 120:92–101 (1989).
O'Meara, R. A. Q., Irish J. Med. Sci. 394:474–479 (1958).
Kinjo, M., et al., J. Cancer 39:15–23 (1979).
Hudig, D., et al., Thromb. Res. 27:321–332 (1982).
Khato, J., et al., GANN 65:289–294 (1974).
Dvorak, H. F., et al., Cancer Res. 43:4434–4441 (1983).
Gouault–Heilmann, M., et al., British J. Haematology 30:151–157 (1975).
Gordon, S. G., et al., Cancer Res. 38:2467–2472 (1978).
Gordon, S. G., et al., Thromb. Res. 6:127–137 (1975).
Gordon, S. G., J. Histochem. Cytochem. 29:457–463 (1981).
Gordon, S. G., et al. U.S. J. Natl. Cancer, Inst. 62:773–776 (1979).
Falanga, A., et al., Biochemistry 24:5558–5567 (1985).
Barrett, A. J., et al. Mammalian Proteases vol. 1 Endopeptidases Academic Press, New York (1980) Sel Reference QP 609.P7M35.
Cavanaugh, P. G., et al., Haemostasis 18:37–46 (1988).
Altieri, D. C., et al., J. Biol. Chem. 264:2969–2972 (1989).
Gastpar, H., J. Med. 8:103–114 (1977).
Gasic, G. J., et al., Proc. Natl. Acad. Sci. USA 61:46–52 (1968).
Gasic, G. J., et al., Int. J. Cancer 11:704–718 (1973).
Pearlstein, E., et al., Cancer Res. 44:3884–3887 (1984).
Skolnick, G., et al., J. Cancer Res. Clin. Oncol. 105:30–37 (1983).

(List continued on next page.)

*Primary Examiner*—Michael P. Woodward
*Assistant Examiner*—Jeffrey S. Parkin
*Attorney, Agent, or Firm*—Ian C. McLeod

[57] ABSTRACT

Thromboembolic complications have been documented in cancer patients and mismatched organ transplant recipients. Procoagulants have been implicated in these processes and may play an additional role in tumor metastases. Two proteins displaying procoagulant activity, with molecular weights of 35,000 and 28,000 daltons, were isolated from human ovarian carcinoma extracts. The amino terminal sequence of the first 12 amino acids of the 35,000 dalton protein was determined to be IKEEHVIIQAEF. This sequence displays 100% homology to the major histocompatibility (MHC) antigen HLA-DR which exists as an heterodimer composed of a 35 kDa and 28 kDa protein. The procoagulant activity was further purified through immunoaffinity column chromatography involving a monoclonal antibody to HLA-DR. The immunoaffinity purified protein enhanced thrombin generation in recalcified normal plasma approximately 20-fold. HLA-DR procoagulant activity was completely abrogated by the addition of *Staphylcoccal aureus* enterotoxin A (SEA).

6 Claims, 7 Drawing Sheets

OTHER PUBLICATIONS

Ivarrson, L., In:Acta Chirurgica Scandinavaia (Eds. Almqvist and Wiskell, Stockholm, (1976). 142:226–230.

Sindelar, W. R., et al., J. Surg. Res. 18:137–161 (1975).

Wood, S., Jr., Cancer Research Laboratory Dept. of Pathology The John Hopkins School of Medicine, Baltimore, 5, Maryland, USA pp. 92–121 (1964).

Foegh, M. L., et al., Urine i–TXB2 in renal allograft rejection, Lancet, 2:431–434 (1981).

Murie, J. A., et al., Transplantation Proc. 19:2219–2220 (1987).

Hidalgo, E. G., et al., Hepato–Gastroenterology 36:529–532 (1989).

Boiskin, I., et al., Am. J. Roentgenology 154:529–531 (1990).

L. H. Toledo–Pereyra Transplant Proc. 6th Floor 20:965–968 (1988).

Rio, B., et al., Blood. 67:1773–1776 (1986).

Arruda, J. A. L., et al., Renal vein thrombosis in kidney allografts, Lancet. 2:585 (1973).

Merion, R. M., et al., Transplant Proc. 17:1746–1750 (1985).

Myers, B. D., et al., N. Engl. J. Med. 311:699–705 (1984).

Ryffel, B., et al., Toxicol Pathol 14:73–82 (1986).

Klintmalm, G. B., et al., Transplantation 32:488–489 (1981).

Atkinson, K., et al Transplantation Proceedings, vol. XV, No. 4, Suppl. 1 pp. 2761–2763 (1983).

Kino, T., et al., J. Antibiotic 40:1256–1265 (1987).

Martel, R. R., et al., J. Physiol. Pharmacol. 55:48–51 (1977).

Dumont, F. J., et al., J. Immunol. 144:251–258 (1990).

Sehgal, S. N., et al., J. Antibiot. 28:727–731 (1975).

Handschwacher et al Science, 226:544–547 (1984).

Harding, M. W., et al., Nature, 341:758–760 (1989).

Dumont, F. J., et al., J. Immunol. 144:1418–1424 (1990).

Metcalfe, S. M., et al., Transplantation 49:798–802 (1990).

Calne, R. et al., Transplant Proc. 19 (suppl 6):63 (1987).

Ubhi, C. S., et al., Transplantation 48:886–887 (1989).

Kappes, D., et al., Ann. Rev. Biochem. 57:991–1028 (1988).

American Journal of Medicine, 89:25–28 (1990). R. L. Edwards et al.

H2N - Ile - Lys - Glu - Glu - His - Val - Ile - Ile - Gln - Ala - Glu - Phe - - -(A)

H2N - Ile - Lys - Glu - Glu - His - Val - Ile - Ile - Gln - Ala - Glu - Phe - - -(B) - - Ref 22

METHOD FOR MEASURING BLOOD PROCOAGULANT ACTIVITY OF HUMAN LEUKOCYTE ANTIGENS

BACKGROUND OF THE INVENTION (1) Field of the Invention

The present invention relates to a method for inhibiting blood procoagulant activity of a histocompatibility antigen ((HLA). In particular, the present invention relates to the use of an enterotoxin to inhibit the activity, particularly in preventing graft rejection coagulation and malignancy induced coagulation.

(2) Prior Art

In 1865, Trousseau observed a high incidence of venous thrombosis in patients with gastric carcinoma and described the syndrome which bears his name (Trousseau, A., In Clinique Medicale de l'Hotel-Dieu de Paris; Paris, Balliere, 3:654 (1865)). A considerable body of evidence supports an association between cancer and thromboembolic disorders (Rickles, F. R., et al., Blood 62:14–31 (1983) ) and elements of the hemostatic system (i.e. platelets, thrombin and fibrin) are proposed as causal for tumor cell metastasis (Weiss, L., et al., Clin. Expl. Metas. 7:127–167 (1989)). Activated platelets may enhance tumor cell adhesion to the vessel wall (Honn, K. V., et al., Biochem. Pharm. 34:235–241 (1985)) and induce endothelial cell retraction (Honn, K. V., et al., FASEB. J. 3:2285–2293 (1989)) while fibrin may aid tumor cells to escape the cellular immune system (Gorelik, E., Cancer Res. 47:809–815 (1987)). Tumor cell activation of platelets and generation of fibrin may require thrombin. Therefore, the identification and isolation of the tumor cell prothrombogenic protein(s) responsible for thrombin generation are of considerable interest.

At least four separate factors are thought to mediate tumor cell induced thrombin generation. The first is tissue factor, a transmembrane glycoprotein and receptor, also associated with normal tissue (Broze, G. J., et al., J. Biol. Chem. 260:10917–10920 (1985); and Buha, A., et al., Proc. Natl. Acad. Sci. USA 83:299–302 (1986)). The second, cancer procoagulant, is a cysteine proteinase that directly activates factor X (Gordon, S. G., et al., J. Clin. Invest. 67:1665–1671 (1981)). The third is a protein termed platelet aggregating activity/procoagulant activity (PAA/PCA) isolated from solid tumors or from tumor cells grown in culture which lacks proteolytic activity and is dependent upon factor X for activity (Cavanaugh, P. G., et al., Thromb. Res. 37:309–326 (1985)). More recently, a factor Xa receptor has been identified on some tumor cells (Sakai, T., et al., J. Biol. Chem. 265:9105–9113 (1990)).

Anticoagulant therapy with warfarin and other coumarins consistently results in a reduction of lung colony formation and spontaneous metastasis strongly suggesting that components of blood coagulation facilitate metastasis. However, warfarin may produce direct effects on tumor cells independent of its action as an anticoagulant (Donati, M. B., et al., In: Recent Advances in Blood Coagulation (Ed. L. Poller), Churchill Livingstone, Edinburgh, pp. 227–259 (1982)). O'Meara and his associates were the first to study a tumor-derived procoagulant activity (O'Meara, R. A. Q., Irish J. Med. Sci. 394:474–479 (1958)). Four separate procoagulants have thus far been identified and are described below.

Tissue factor—Kinjo et al (Kinjo, M., et al., J. Cancer 39:15–23 (1979)), Hudij and Bajaj (Hudig, D., et al., Thromb. Res. 27:321–332 (1982)), Khato, et al. (Khato, J., et al., GANN 65:289–294 (1974)), and Dvorak, et al. , (Dvorak, H. F., et al., Cancer Res. 43:4334–4342 (1983)) have shown that tumor cell induced coagulation required FVII suggesting that thromboplastin was responsible for activity. This has been substantiated by showing that antibodies to human brain thromboplastin neutralize the procoagulant activity of human leukemic promyelocytes (Gouault-Heilmann, M., et al., J. Haematol. 30:151–157 (1975)). Tissue factor has been purified only from normal brain tissue by affinity chromatography (Broze, G. J., et al., J. Biol. Chem. 260:10917–10920 (1985); and Guha, A., et al., Proc. Natl. Acad. Sci. USA 83:299–302 (1986)). It has a molecular weight of 43,000, requires lipids for activity, and catalyses the hydrolysis of factor IX and X by factor VIIa.

Cancer procoagulant—Gordon and co-workers (Gordon, S. G., et al., Cancer Res. 38:2467–2472 (1978); Gordon, S. G., et al., J. Clin. Invest. 67:1665–1671 (1981); Gordon, S. G., et al. , Thromb. Res. 6:127–137 (1975); Gordon, S. G., J. Histochem. Cytochem. 29:457–463 (1981); Gordon, S. G., et al., J. Natl. Cancer. Inst. 62:773–776 (1979); and Falanga, A., et al., Biochemistry 24:5558–5567 (1985)) purified cancer procoagulant (CP) from a soluble extract of rabbit V2 carcinoma cells. Purified CP has a molecular weight of 68,000 with an isoelectric point of 4.8. CP(i) requires phospholipid for activity (ii) activates factor X and this proteolytic activity can be inhibited with iodoacetamide and mercury and reactivated with potassium cyanide, dithiothreitol and EDTA, suggesting that it may be a cysteine proteinase and (iii) is stable in alkaline pH (Barrett, A. J., et al., Mammalian Proteases Vol. 1 Endopeptidases 416 pp. Academic Press, New York (1980)); thus, it apears to be a non-lysosomal cysteine proteinase.

Platelet aggregating activity/procoagulant activity (PAA/PCA)—Cavanaugh et al have shown that yet another procoagulant protein PAA/PCA is produced by tumor cells. The size of this protein varies with species, the murine adenocarcinoma protein has a molecular weight of 51,000 (Cavanaugh, P. G., et al., Thromb. Res. 37:309–326 (1985)) while the rat Walker 256 carcinosarcoma produces a protein of 58,000 daltons (Cavanaugh, P. G., et al., Hemostasis, 18:37–46 (1988)). PAA/PCA (i) does not have any proteolytic activity and (ii) procoagulant activity is observed only after reconstitution with phospholipids.

Factor Xa receptor on tumor cells—Recent studies by Sakai and Kisiel (Sakai, T., et al., J. Biol. Chem. 265:9105–9113 (1990)) and Altieri and Edgington (Altieri, D. C., et al., J. Biol. Chem. 264:2969–2977 (1989)) provide evidence for the presence of a novel prothrombinase complex in some tumor cells. Radio-iodinated FXa binds specifically to a human hepatocellular carcinoma cell line (HepG2) which constitutively synthesizes a factor V/Va molecule and to a human bladder carcinoma (J82) which does not synthesize factor V/Va. Pretreatment of J82 cells with anti-human V IgG had no significant effect on binding of FXa or prothrombin activation. However, pretreatment of HepG2 cells with FV antibodies inhibited prothrombin activation in a dose dependent manner without inhibiting FXa binding. When both cells were incubated with exogenous FVa, the binding of FXa to either HepG2 or J82 cells were only marginally affected. These studies suggest FXa binding to sites proximal to but independent of cell surface FVa.

Thus, procoagulant activities associated with tumor cells or attached stromal cells would promote the generation of thrombin. Thrombin is a potent and physiologic activator of platelets and it would be intuitive that platelets would be activated in the vicinity of tumor cells. Indeed, intravenously injected tumor cells were observed to induce platelet aggregation (Gastpar, H., J. Med. 8:103–114 (1977)). Thrombocytopenia induced by neuraminidase or antiplatelet antiserum results in decreased lung colony formation from tail vein-injected tumor cells (Gasic, G. J., et al., Proc. Natl. Acad. Sci. USA 61:46–52 (1968); Gasic, G. J., et al., Int. J. Cancer 11:704–718 (1973); Pearlstein, E., et al., Cancer Res. 44:3884–3887 (1984); Skolnick, G., et al., J. Cancer Res. Clin. Oncol. 105:30–37 (1983); Ivarrson, L., In:Acta Chirurgica Scandinavia (Eds. Almqvist and Wiskell), Stockholm, (1976); and Sindelar, W. R., et al., J. Surg. Res. 18:137–161 (1975)) and spontaneous metastasis from subcutaneous tumors (Pearlstein, E., et al., Cancer Res. 44:3884–3887 (1984); and Wood, S., Jr., et al., Bull. Schweiz. Akad. Med. Wiss. 20:92–121 (1964)) suggesting a role for platelets in metastasis. Fibrin adhered to tumor cells may also play a role in tumor growth and invasion (Gastpar, H., J. Med. 8:103–114 (1977)).

Numerous examples abound in the literature providing strong evidence that there is a definite association between the incidence of thromboembolic complications and onset of tissue transplant rejection. Foegh and coworkers (Foegh, M. L., et al., Urine i-TXB2 in renal allograft rejection, Lancet. 2:431–434 (1981)) first observed an increase of thromboxane B2 preceeding the onset of renal graft rejection. There are now several papers on the association of thromboembolic disorders with liver (Blumhardt, G., et al., Transplantation Proc. 19:2219–2220 (1987); and Hidalgo, E. G., et al., Hepato-Gastroenterology. 36:529–532 (1989)), pancreatic (Boiskin, I., et al., Am. J. Roentgenology. 154:529–531 (1990); and Soon-Shiong, P., et al., Transplant Proc. 20:965–971 (1988)) and bone marrow (Rio, B., et al., Blood. 67:1773–1776 (1986)) graft rejection.

Some success has been achieved in engraftment of renal transplants by treatment of recipients with cyclosporin A (CsA). This immunosuppressive regimen however does not overcome the small number of allografts lost in early post-transplantation as a result of renal artery and vein thrombosis (Arrunda, J. A. L., et al., Renal vein thrombosis in kidney allografts. Lancet. 2:585 (1973)). There have also been reports of an increased incidence of thrombosis in patients immunosuppressed with CsA (Merrion, R. M., et al., Transplant Proc. 17:1746–1750 (1985)). An added complication is nephrotoxicity (Myers, B. D., et al., N. Engl. J. Med. 311:699–705 (1984); and Ryffel, B., et al., Toxicol Pathol 14:78 (1986)) and hepatotoxicity (Klintmalm, G. B., et al., Transplantation 32: 488–489 (1981); and Roger, S., et al., Transplant Proc. 15:2761–2767 (1983)) caused by high doses of CsA.

More recently, two additional drugs have become available for the treatment of graft rejection. FK506, an antibiotic of the macrolide family isolated from *Streptomyces tsukubaensis* (Kino, T., et al., J. Antibiotic 40:1256–1265 (1987)) is about 100 to 500 times more potent than CsA. Rapamycin, which was recently shown to have immunosuppressive effects (Martel, R. R., et al., J. Physiol. Pharmacol. 55:48- (1977)) was originally identified for its antifungal activity (Dumont, F. J., et al., J. Immunol. 144:251–258 (1990)), is a structural analog of FK506 isolated from *Streptomyces hygroscopicus* (Sehgal, S. N., et al., J. Antibiot. 28:727- (1979)).

All three immunosuppressants exert their effects by binding to proteins termed immunophilins with high affinity. CsA binds to human cyclophilin (Handsschumacher, R. D., et al., Science, 226:544–547 (1984)) and both FK506 and rapamycin bind to human FK506 binding protein (FKBP) (Harding, M. W., et al., Nature, 341:758–760 (1989)). It has been suggested that FK506 like CsA inhibits a T cell receptor mediated signal transduction pathway that results in the transcription of early T cell activation genes, including interleukin-2 (IL-2). (e). Although rapamycin binds to FKBP, it has no effect on IL-2 production. In fact it appears to behave antogonistically to FK506 (Dumont, F. J., et al., J. Immunol. 144:1418–1424 (1990)). Furthermore, drug combinations of FK506 and CsA, FK506 and rapamycin and rapamycin and CsA are not synergistic (Metcalf, S. M., et al., Transplantation. 49:798–802 (1990)). Recent studies have also shown that FK506 may have diabetogenic effects (Calne, R., et al., Transplant Proc. 19 (suppl 6):63 (1987)). It would appear that these immunosuppressants would have no influence on thrombotic consequences imposed by tissue transplants. Indeed one clinical study showed that administration of subcutaneous heparin together with a regimen of CsA significantly reduced thromboembolic complications and prolonged graft survival (Ubhi, C. S., et al., Transplantation 48:886–887 (1989)).

It has been thought that other factors may mediate coagulation in graft rejection and tumor cell induced coagulation. To date, such other factors and a method of inhibiting the factor has been unknown.

OBJECTS

It is therefore an object of the present invention to provide a method for inhibiting HLA which at elevated levels induces coagulation, either by HLA in metastatic tumor cells, HLA induced by chemotherapy or by HLA in grafts to cause rejection. In particular the presentation provides a method which is simple and economical. These and other objects will become increasingly apparent by reference to the following description and the drawings.

IN THE DRAWINGS

FIG. 1A shows the results of Q-Sepharose column chromatography of material from human ovarian tumors which were metastatic. The plasma membrane fraction containing 0.25% CHAPS (3-cholamidopropyldimethyl-amminio-1-propane sulfonate) was applied onto a 1 cm×30 cm column equilibrated in 25 mM Tris-HCl buffer, pH 7.5, containing 0.25% CHAPS. The column was washed with two column volumes of starting buffer to remove unbound protein and developed with a 0.0–1.0M NaCl gradient in 120 ml at a flow rate of 60 ml/hr. The eluate was fractionated into 5 ml volumes. Absorbence at 280 nm is shown as open circles. Procoagulant activity is shown as closed circles. As shown in FIG. 1a, the activity eluted in a symmetric peak. The active fractions were pooled, dialyzed against 10 mM KH$_2$PO$_4$/K$_2$HPO$_4$ buffer, pH 7.2 and applied onto a hydroxyapatite column (Source: BioRad, Rockville Center, N.Y.). Activity was detected in the protein fraction which did not bind to this column. The active sample was then delipidated as described hereinafter. Finally, the protein preparation was dialyzed and applied onto a Mono Q column as shown in FIG. 1b.

Figure 1B:
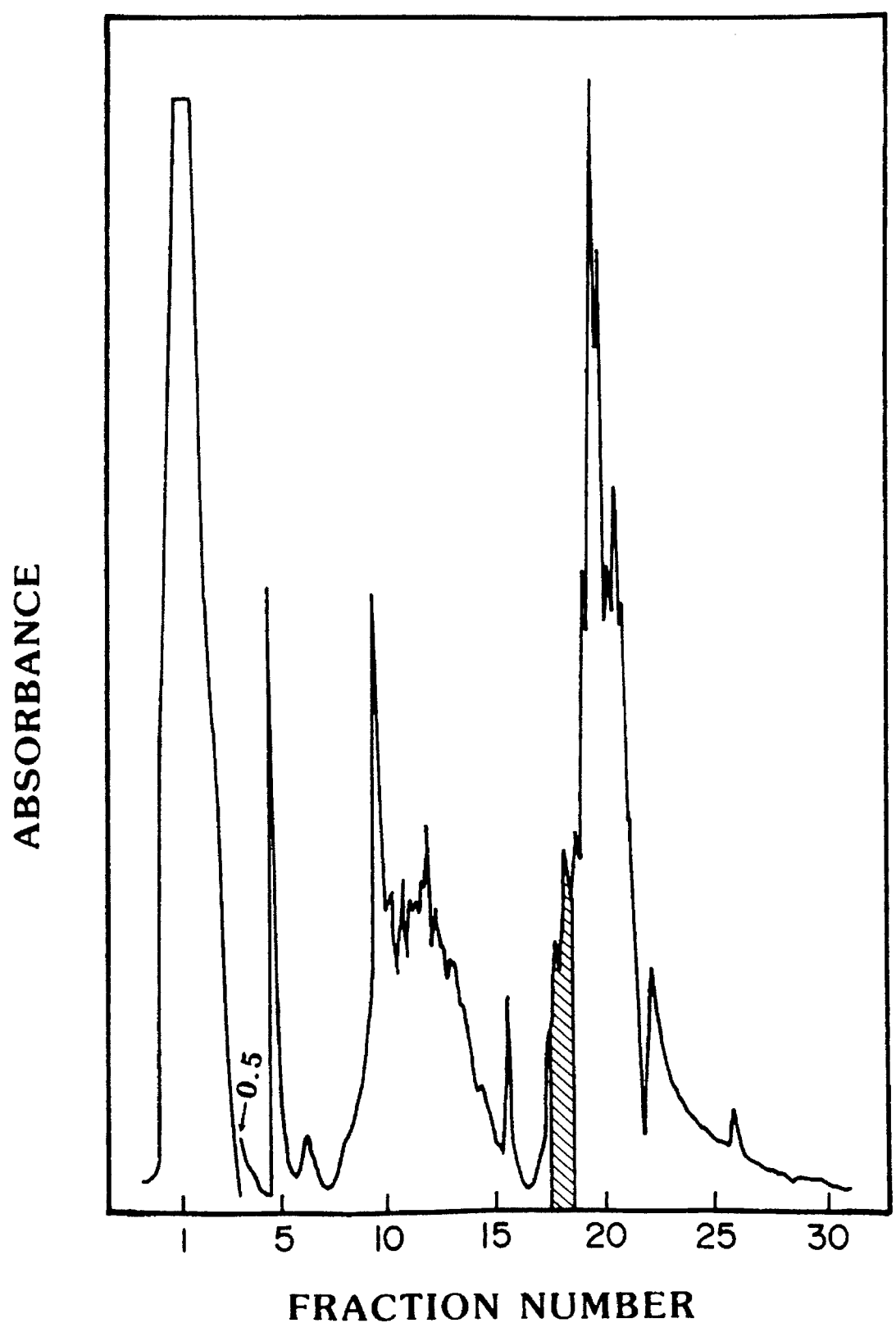

FIG. 1B shows the Mono Q column chromatography. The column was equilibrated in 25 mM Tris-HCl buffer, pH 8.2. Protein isolated from the hydroxyapatite column was delipidated. There was therefore no further requirement for detergents in this and subsequent steps. The column was washed with two column volumes to remove unbound protein and developed with a 0.0–1.0M NaCl gradient in 120 ml at a flow rate of 60 ml/hr. The eluate was fractionated into 5 ml volumes. Most activity (~75%) was seen in fraction 18

(shaded area). It was obvious that the activity resided in the ascending portion of another major protein peak. Some activity was also present in fractions 19 through 23 but they were not included, thus reducing contaminating proteins.

Figure 1C:
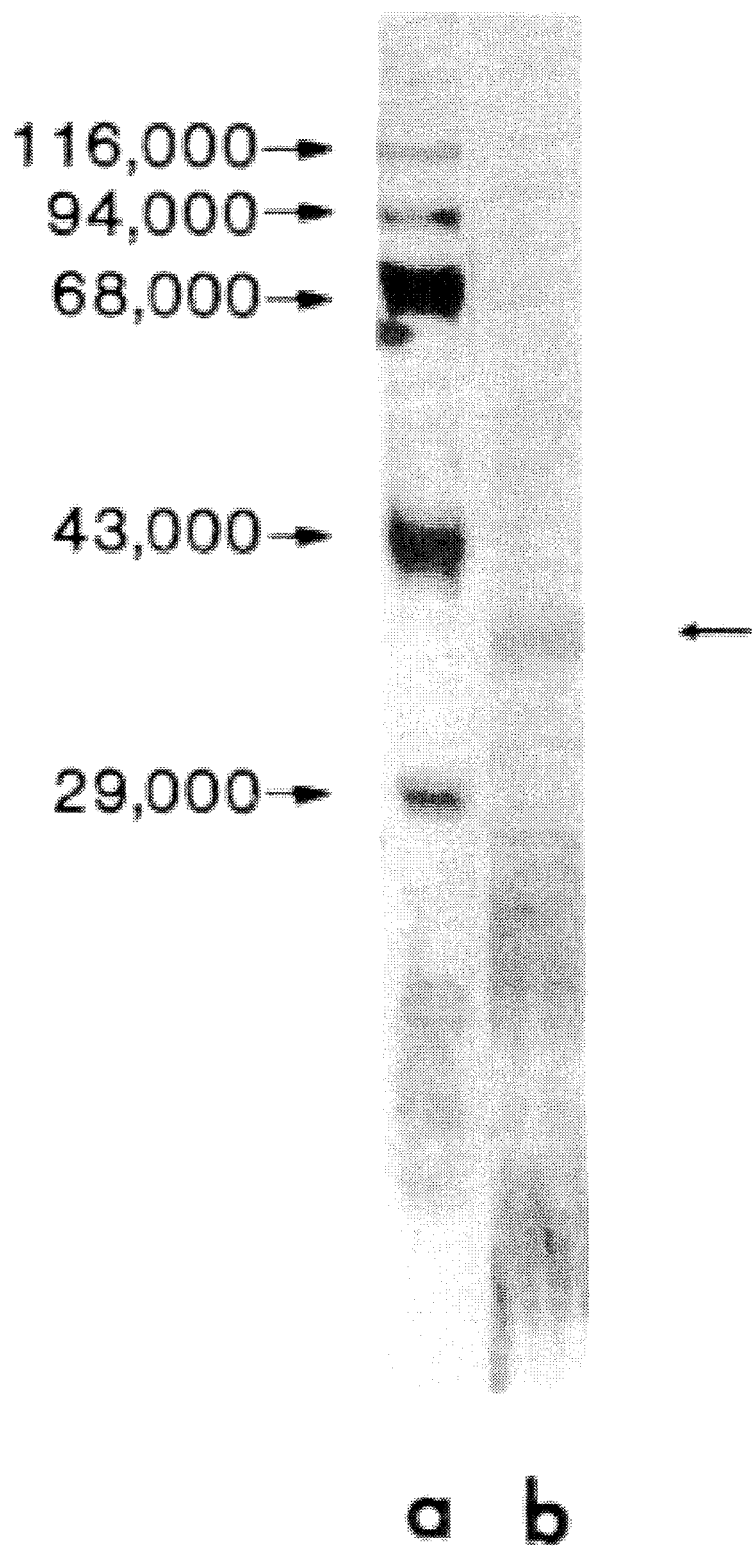

FIG. 1C shows the slab gel electrophoretic pattern of the procoagulant protein preparation after the Mono Q column chromatography of FIG. 1b in the presence of sodium dodecyl sulfate (lane a) and beta-mercaptoethanol (lane b). Slab gel electrophoresis with SDS was carried out according to Laemmli (Laemmli, U.K., Nature (London). 227:680–685 (1970)). Stacking and separating gels were 4% and 9% acrylamide, respectively. Samples were diluted 1:2 in the upper gel buffer containing 2% (w/v) SDS and heated to 100° C. for 5 minutes. Gels were fixed and stained with 0.25% Coomassie blue in 50% methanol and 10% acetic acid. The protein band of 35,000 daltons (arrowed) was excised and sequenced. Another band of 28,000 was also observed but not sequenced. Molecular weight markers beta-galactosidase (116,000), phosphorylase a (94,000), bovine serum albumin (68,000), ovalbumin (43,000) and carbonic anhydrase (29,000) are shown in lane a.

Figures 2, 4:
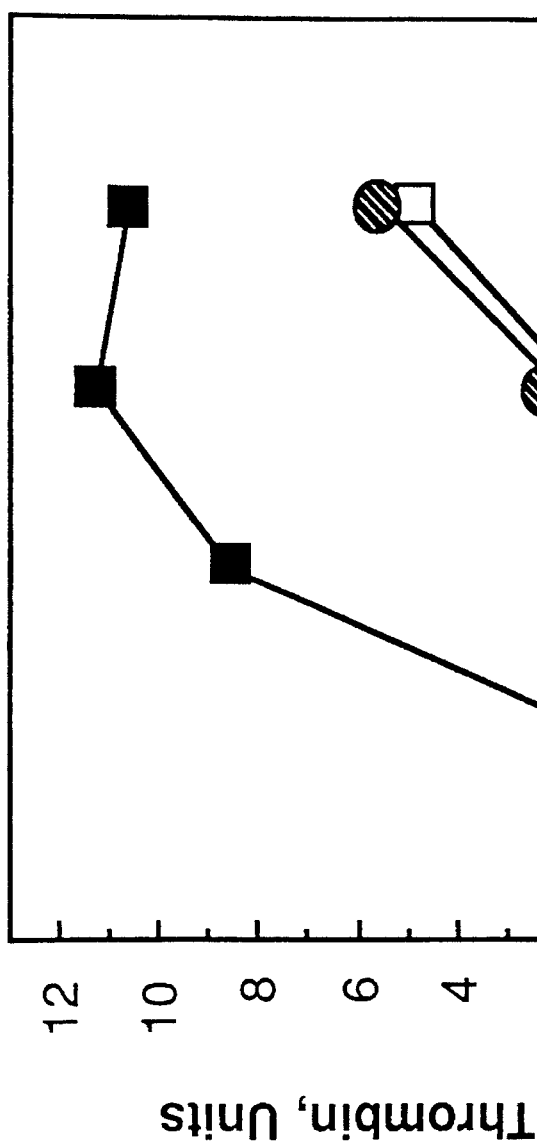

FIG. 2 shows a comparison of the amino-terminal sequence of the first 12 residues of the 35,000 dalton protein isolated from Human Ovarian Carcinoma (A) with that of the HLA-DR protein (B: see Kappes, D, et al., Ann. Rev. Biochem. 57:991–1028 (1988)). It was concluded that these proteins were similar.

Figure 3A:
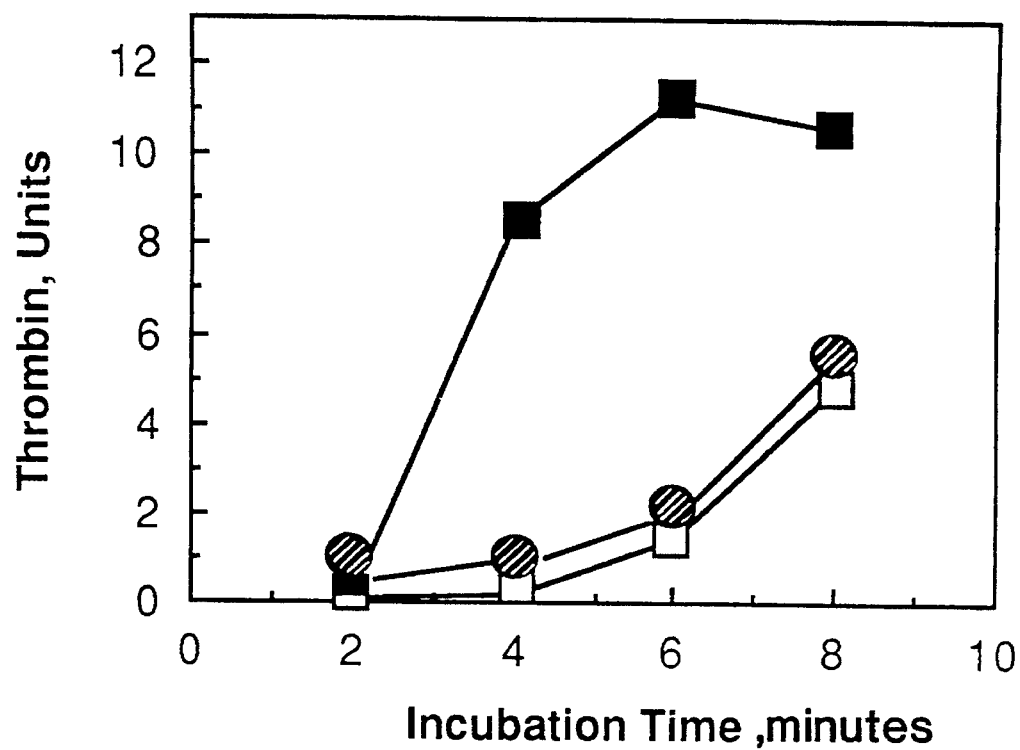
Figure 3B:
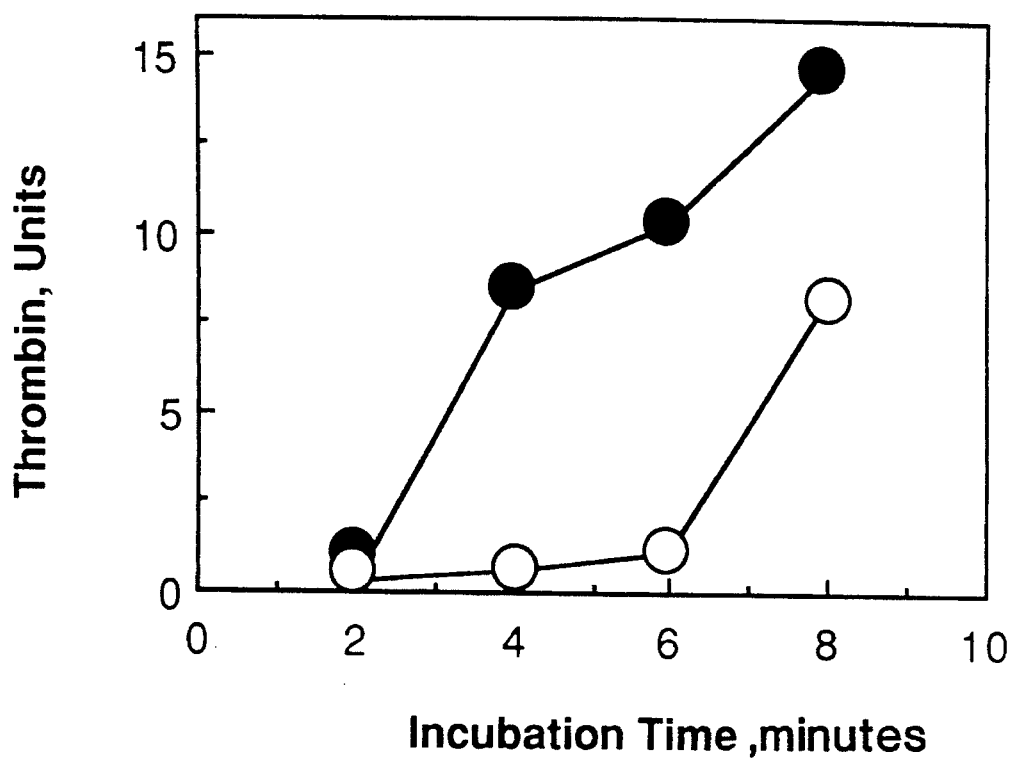

FIGS. 3A and 3B show a time course of thrombin generation in normal human plasma (FIG. 3A) and plasma deficient in Factor VII (FIG. 3B) in the presence (closed symbols) and absence (open symbols) of HLA-DR. The concentration of HLA-DR was 115 nM (Read, S. M., et al., Anal. Biochem. 116:53–64 (1981)). These results are representative of ten different experiments using three different preparations of immunoaffinity purified HLA-DR and show that HLA-DR causes thrombin generation.

FIG. 4 shows the effect of Staphylococcal enterotoxin A on procoagulant activity of HLA-DR. Experiments were carried out exactly as described in FIGS. 3A and 3B except that normal plasma was preincubated with HLA-DR■, HLA-DR and SEA●, or with nothing □ which was the control. SEA completely inhibited the HLA-DR.

Figure 5:
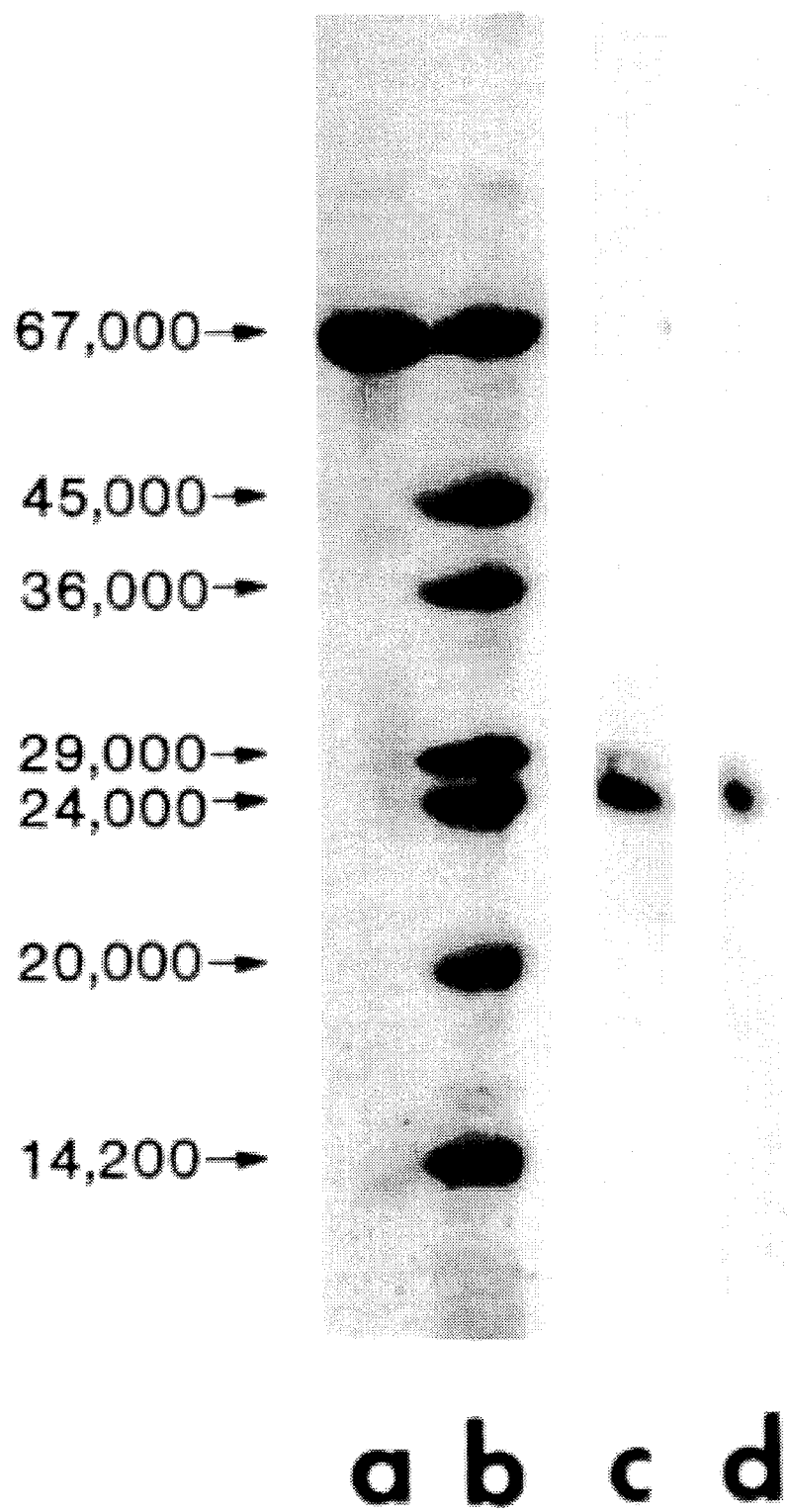
Figure 6A:
Figure 6B:
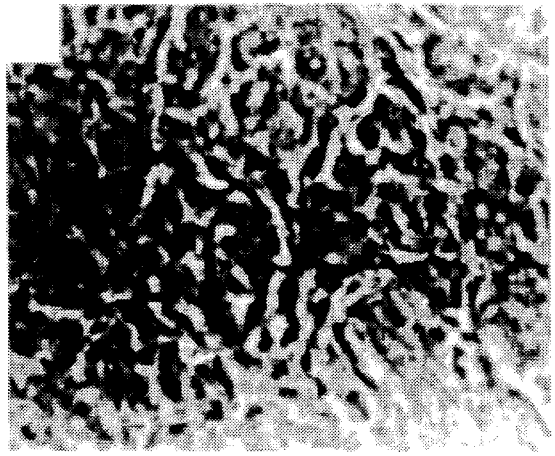
Figure 6C:
Figure 6D:
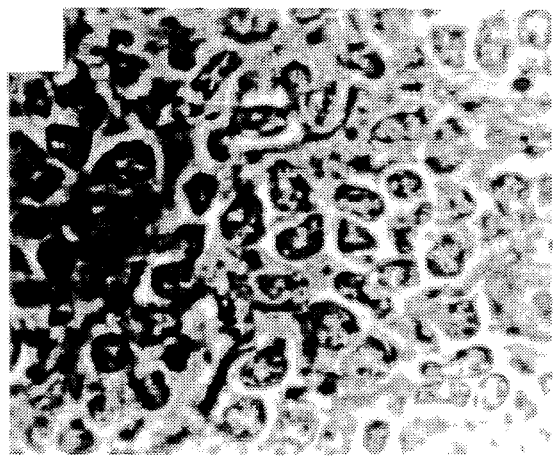

FIG. 5 in lanes a, b, c and d show SDS-Page separation of an albumin standard (5a); molecular weight standards (5b) including

| Standard | MW |
|---|---|
| albumin | 67,000 |
| ovalbumin | 45,000 |
| dehydrogenase | 36,000 |
| carbonic anhydrase | 29,000 |
| soybean trypsin inhibitor | 20,100 |
| lactalbumin | 14,200 |

Authentic HLA-DR, purified using antibodies (5c); and evidence that plasma proteins bound to a solid phase binds HLA-DR in the presence of calcium chloride (5d). In lane (d) plasma was coupled onto a solid phase and a HLA-DR containing solution was passed over the column in the presence of calcium. After washing the column to remove unbound protein, the column with EDTA was washed to remove any calcium dependent bound protein. The bound protein was electrophoresed on a gel, transferred electrically onto a membrane (Western blot) and protein visualized by monoclonal antibody to HLA-DR.

FIGS. 6A to 6D are microscopic photographs of lung carcinoma cells stained with fluorescent labeled monoclonal antibody specific to HLA-DR (FIG. 6A); unstained phase contrast microscopy of lung carcinoma cells (6B); T-cell lymphocytes which are immuno-stained with antibody specific for HLA-DR (6C); and unstained phase contrast microscopy of T-cell lymphocytes (6D).

GENERAL DESCRIPTION

The present invention relates to a method for inhibiting a blood procoagulant activity of a histocompatibility antigen (HLA) selected from the group consisting of HLA-DR and HLA-DQ and subunits thereof which comprises: providing an amount of a polypeptide selected from the group consisting of an enterotoxin and active peptide subunits thereof with the antigen so that the antigen is bound by the enterotoxin to eliminate the blood procoagulant activity.

Further, the present invention relates to a composition for inhibiting a blood procoagulant activity of a human leukocyte antigen selected from the group consisting of HLA-DR and HLA-DQ and subunits thereof which comprises in admixture: a polypeptide selected from the group consisting of *Staphylococcal aureus* enterotoxin A, B, C1, C2, C3, D and E, Toxic Shock Syndrome toxin (TSST1), *Streptococcus pyogenes* A and C and *Staphylococcal aureus* exfoliating toxins A and B and an active peptide subunit thereof which binds the antigen; and a sterile carrier for the polypeptide.

Where HLA activity is to be removed from the blood, such as when produced by a metastatic tumor or by chemotherapy, it is preferred that the blood be treated externally of the patient in a column containing bound endotoxin. In this case the HLA alone or with the metastatic cell is preferably bound to the column and the blood is then returned to the body. Another method is the intervenous injection of the endotoxin in a sterile solution into the blood at very low levels (1 to 10 nanomoles per ml of blood). Care must be taken that the levels of the endotoxin are less than would poison the patient.

Where the HLA activity is at an incision for a graft, then the preferred method is to apply the endotoxin topically at the incision in a sterile solution, preferably an aqueous solution. The solution preferably contains between about 1 to 10 nanomoles of the endotoxin per ml. The solution is applied in very small amounts to the incision, preferably between about 2 and 5 AU per sq. mm of the incision.

The toxins are used in an amount which binds the HLA, preferably between about 1 and 10 arbitrary units (AU) per unit of HLA. Generally a solution containing between about 1 and 10 AU/ml of the toxin is used to inhibit the HLA. The toxins preferably selectively bind HLA-DR and HLA-DQ. An "arbitrary unit" is defined as the amount of toxin required to inhibit 1 AU of HLA. An AU of HLA is that amount of HLA which produces a detectable amount of blood coagulation in vitro in 1 ml of blood.

The binding proteins which are preferred are toxins which bind HLA. The toxins are selected from the group consisting of *Staphylococcus aureus* endotoxin A, B, C1, C2, C3, D and E, Toxic Shock Syndrome bacterial toxin, *Streptococcus pyogenes* A and C, *Staphylococcus aureus* exfoliating toxins A and B as well as active subunits of these toxins which selectively bind the HLA. Preferred is *S. aureus* toxin A (SEA).

The gene products of the Major Histocompatibility Complex (MHC) are some of the main proteins involved in the ability of cells to respond to foreign antigens. Of the two classes, the Class I proteins are known as the transplantation antigens while the Class II proteins are referred to as the immune response proteins (Kappes, D, et al., Ann. Rev. Biochem. 57:991–1028 (1988)). Structural studies have revealed that each class of protein exists as an alpha-beta heterodimer on the surface of a variety of cell types including leukocytes, lymphocytes, macrophages and monocytes. In the human the alpha and beta chains of class II heterodimer have molecular weights of 33,000 and 28,000, respectively (Lee, J. S., et al., Nature. 299:750–752 (1982)). It has been found that the 35,000 and 28,000 dalton proteins of HLA-DR isolated either by conventional methods or by immunoaffinity chromatography enhanced thrombin generation in normal plasma. Authentic HLA-DR also had procoagulant activity and thus strengthened these observations. Interestingly, the 35,000 and 28,000 proteins individually express procoagulant activity when electrophoresed on SDS-PAGE followed by Western blot transfer to immobilon P membrane (transfer to this membrane ensures removal of sodium dodecyl sulfate which permits not only sequence analysis but also testing in the bioassay). This finding suggests that the alpha-beta heterodimer complex is not a prerequisite for procoagulant activity. The alpha chain shares 35% homology with the beta chain (Lee, J. S., et al., Nature. 299:750–752 (1982)), thus it is believed that these areas of sequence homology contain the peptides with the procoagulant activity. Both the alpha and beta chains span the membrane. Each chain consists of two main extracellular domains of 90–100 amino acids, a transmembrane region of 20–25 amino acids and an intracellular segment of 8–15 amino acid residues. The procoagulant activity is present in intact tumor cells (Chelladurai, M., et al., Proc. Am. Ass. Can. Res. 29:68a (1988)) suggesting that the procoagulant activity resides with the extracellular moiety of the HLA-DR molecule. Further strength is given to this from the observation that intact T cells specifically bind radiolabelled staphylococcal enterotoxin A (SEA). The procoagulant activity of HLA-DR is completely inhibited by SEA which is specific to HLA-DR.

There are three subsets of the Class II antigens designated DR, DP and DQ. These are expressed in all human haplotypes. The DR subset has been reported to be present in highest concentration (Gorga, J., et al., J. Biol. Chem. 262:16087–16094 (1987)). This is one explanation for the selective isolation of the DR subset over DP and DQ.

The possible contamination of preparations with tissue factor was of concern. It should be noted that HLA-DR was immunochemically purified hence reducing any interference from contaminants. More importantly, preparations of human ovarian carcinoma used to isolate HLA-DR had the same procoagulant activity in the presence or absence of anti-human tissue factor. These findings coupled with the observation that SEA inhibits the procoagulant activity of HLA-DR clearly establish that the procoagulant activity of HLA-DR isolated from human ovarian carcinoma is unrelated to tissue factor.

A number of nonlymphoid cancers such as colorectal (Daar, A. S., et al., J. Immunol. 129:447–449 (1982) and melanoma (Winchester, R. J., Proc. Natl. Acad. Sci. USA. 75:6235–6239 (1978)) have been shown to express the Class II antigens. Basham and Merigan (Basham, T. Y., et al., J. Immunol. 130:1492–1494 (1983)) have observed a five to six-fold increase in the synthesis and expression of HLA-DR in melanoma cells upon stimulation by interferon-gamma. They have therefore suggested that these antigens may be involved in immunologic interactions between the host and the tumor. The molecular mechanisms by which the histocompatibility antigens mediate the immune response in normal and cancer states needs to be delineated. In addition to its immunological function, the class II antigen, HLA-DR also contains procoagulant activity. It is not known if the procoagulant activity of HLA-DR has any role in the immune response.

SPECIFIC DESCRIPTION

Materials and Methods

Human ovarian carcinoma was selected since ovarian tumors have high levels of procoagulant activity and adequate amounts of starting material were available. The procoagulant protein finally isolated had properties different from those ascribed to the other tumor procoagulants. The protein isolated was the DR subset of the Class II major histocompatibility antigens (MHC).

EXAMPLE 1

Human ovarian tumors were provided by The National Disease Resource Interchange, Philadelphia, Pa. and The Cooperative Human Tissue Network, Columbus, Ohio. All other chemicals were purchased from Sigma Chemical Company, St. Louis, Mo. unless otherwise stated.

Isolation of light mitochondrial fraction. This fraction was isolated according to the modified method (Rozhin, J., et al., Cancer Res. 47:6602–6628 (1987)) of DeDuve et al (DeDuve, C., et al., Biochem J. 60:604–615 (1955)). All isolation procedures were carried out at 4° C. Fresh frozen tumor, 30–40 gm tumor wet weight, was ground in a food processor, suspended in 10 volumes of 25 mM MES buffer pH 6.5 containing 5% sucrose, 0.9% NaCl, 10 mM EDTA, 1 mM Phenylmethylsulfonyl fluoride (PMSF), $10^{-6}$M trans-Epoxysuccinyl-L-leucylamido-(4-guanidino)butane (E-64) and 1 mM leupeptin and homogenized by ten strokes through a Potter-Elvejhem homogenizer. The cell homogenate was passed through a muslin gauze and the filtrate centrifuged at 6700×g for 7 minutes in a Beckman Ti45 rotor. The pellet containing the nuclear and mitochondrial fraction was resuspended in the MES buffer and the centrifugation repeated at 6700×g for 7 minutes. The supernatants were pooled and recentrifuged at 15,100×g for 19 minutes in the same rotor. The resulting pellet, the light mitochondrial fraction, was resuspended in 25 mM Tris-HCl buffer, pH 8.2. CHAPS was added to the suspension to obtain a final concentration of 0.25%.

Isolation of Procoagulant Protein. The light mitochondrial fraction (i.e. plasma membrane plus lysosomal) was applied onto a 1 cm×30 cm Q-Sepharose (Pharmacia, Piscataway, N.J.) column equilibrated in 25 mM Tris-HCl buffer, pH 7.5, containing 0.25% CHAPS. The column was developed as detailed in reference to FIG. 1a. Activity was quantitated in a newly developed coagulation assay described below. Active fractions were pooled, dialyzed against 10 mM $KH_2PO_4/K2HPO_4$ buffer pH 7.2 containing 0.25% CHAPS and applied onto a hydroxyapatite (Bio-Rad, Rockville Center, N.Y.) column equilibrated in the same buffer. Procoagulant activity which eluted with the unbound fraction was dialyzed extensively against distilled water to remove CHAPS and lyophilized. The dried powder was resuspended in a minimal volume of 25 mM Tris-HCl buffer, pH 8.2 and lipid extracted from the preparation by vortexing each ml of reconstituted protein sample with 0.7 ml of LipiFree™ (1,1,2-Tri-chlorotriluoroethane; Genex Corporation, Gaithersburg, Md.). The cloudy suspension was centrifuged at 1000×g for 20 minutes. The aqueous upper layer, containing the procoagulant activity, was carefully siphoned off, applied onto a Mono Q column (Pharmacia) and developed as described in reference to FIG. 1b.

Active fractions analyzed on SDS-PAGE (Laemmli, U.K., Nature (London) 227:680–685 (1970)) were found to have at least four protein bands. The preparation was then electrophoresed in duplicate lanes on SDS-PAGE and the proteins transferred onto an immobilon P membrane. One lane was stained with Coomassie blue and destained to identify the protein bands. All corresponding bands in an unstained lane were excised and assayed for procoagulant activity. This procedure identified proteins with procoagulant activity in the stained lane and were excised for sequence analysis. Sections of membrane which contained no protein were also tested in controls. Protein microsequence analysis was obtained by automated Edman chemistry on an Applied Biosystems gas phase sequenator, Model 470, with on line HPLC (Model 120), a Nelson Analytical chromatography Data System and a 900 A control/data system. Levels below 100 picomoles have been sequenced routinely for proteins transferred by electroblotting to polyvinyl difluoride (PVDF; eg Immobilon P, Millipore Corporation, Burlington, Mass.) membranes.

Lectin Affinity Chromatography. This procedure was as previously described (Roitt, I., et al., Anal. Biochem. 116:53–64 (1985)). Light mitochondrial fraction from human ovarian carcinoma, solubilized in 1% Triton X-100, was applied onto the lectin-Sepharose column equilibrated with 50 mM HEPES buffer pH 7.5 containing 1 mM $CaCl_2$ and 1 mM $MnCl_2$ and washed to remove all unbound protein. Bound protein was eluted with 0.1M methyl alpha-D-mannopyranoside in HEPES buffer, pH 7.5. The eluate was dialyzed extensively against distilled water and lyophilized.

Immunochemical Isolation using Anti-HLA-DR column. Monoclonal antibody to HLA-DR (AMAC, Inc. Westbrook, Me.) was reconstituted in $H_2O$, dialyzed against 0.1M sodium bicarbonate buffer pH 8.3 containing 0.5M NaCl (coupling buffer) and coupled to CNBr-activated Sepharose 4B suspended in the same buffer. The protein isolated from the lectin column was applied to the immunoaffinity column. The column was washed with at least three column volumes to remove unbound protein and bound protein was eluated with 0.1M Glycine/HCl buffer, pH 2.5. Eluted fractions were dialyzed extensively against $H_2O$ and lyophilized. Protein concentration was determined according to the Bradford method (Read, S. M., et al., Anal. Biochem. 116:53–64 (1981)).

Coagulation Assay. Plasma was rendered free of fibrinogen with the aid of ancrod defibrilating enzyme, Sigma Chemical Co., St. Louis, Mo. (Seligson, D., Hematology, Vol III:301 (1980)). The resulting clot was removed and the remaining plasma activated (5 min, 25° C.) by addition of calcium chloride (6.25 mM final concentration ) in the presence or absence of the tumor procoagulant. The reaction was stopped at various timed intervals with the addition of 2.5 mM EDTA (final concentration). Thrombin generated in these assays was measured using S 2238 (H-D-Phenylalanyl-L-pipecoyl-L-arginine-o-nitroanilide dihydrochloride), a thrombin-specific chromogenic substrate (Sandberg, H., et al. Throm. Res. 14:113–124 (1979)). The color generated after addition of S2238 was stopped with 50% acetic acid and absorbence measured in a Bio-Tek EL312 Microplate Reader. The unit of procoagulant activity is defined as the amount of protein required to generate one unit of thrombin per min. For a standard curve, known amounts of thrombin were used to hydrolyze S2238 and the rate of change of optical density per minute versus thrombin concentration was obtained. Rabbit thromboplastin used, under the same conditions, in controls and was found to generate 5.5 units of thrombin per minute per mg protein. By comparison, immunochemically purified HLA-DR generated 435 units of thrombin per min per mg protein. This represents a 79-fold higher activity compared to thromboplastin. Anti-human tissue factor antibody did not have any effect on the procoagulant activity of our preparations of human ovarian carcinoma. The effect of HLA-DR on thrombin generation in commercially available factor-deficient plasmas (Helena Laboratories, Beaumont, Tex.) were also tested.

The Western blot protein transfer procedure is a modification of the Bio-Rad method. All buffers were made with Milli-Q (Millipore Corporation, Burlington, Mass.) grade water. Proteins in a polyacrylamide gel slab were electrically transferred (35 V constant for 16 h) onto an Immobilon P membrane (Millipore) using a Bio-Rad Trans-Blot apparatus and 25 mM Tris, 200 mM glycine, 20% methanol, pH 8.3 as the transfer buffer. The membrane was stained for 15 min with 0.25% Coomassie blue in 50% methanol. The membrane was then destained in 90% methanol.

Molecular Weight

FIG. 5 shows the molecular weight sizing of HLA-DR from plasma. The molecular weight of the alpha-chain is 35,000 and the beta-chain is 28,000.

Lymphocyte Cell Staining

FIG. 6 shows the presence of HLA-DR in lung carcinoma cells and T-cell lymphocytes. The T-cells exhibit positive staining while the tumor cells exhibit extensive staining. The treatment of the HLA-DR with SEA inhibits staining caused by the excess HLA-DR of these tumor cells.

RESULTS

Initially, the isolation of procoagulant activity was attempted using conventional methods. A plasma membrane enriched fraction was isolated since it was observed that (i) intact tumor cells were able to significantly reduce clotting time in recalcified plasma and (ii) in subcellular fractionation studies the plasma membrane of the human ovarian carcinoma contained more than 85% of the total procoagulant activity (Chelladurai, M., et al., Proc. Am. Ass. Can. Res. 29:68a (1988)). Furthermore, our studies have shown that the expression of procoagulant activity was increased as much as 20,000 fold greater in murine tumor tissues compared to normal cells (Chelladurai, M., et al., Proc. Am. Ass. Can. Res. 29:68a (1988)). The detergent CHAPS was employed to solubilize the light mitochondrial fraction and in buffers for the first ion-exchange chromatography and hydroxyapatite column. Subsequently, all procedures were carried out in the absence of detergent. In order to reduce interference from lipids in the membrane fraction, the material containing procoagulant activity was treated with Lipi-free™. Following the isolation protocol described in the legends to FIGS. 1a and 1b, the protein yields were poor and homogeneity was not achieved. Therefore, the semipurified protein preparation was separated on SDS-PAGE, transferred onto an immobilon P membrane and Coomassie stained to identify the protein bands (FIG. 1c). Two protein bands of 35,000 and 28,000 daltons were found to have procoagulant activity. The corresponding stained bands were then excised and used for sequence analysis. The sequence of the first 12 residues of the 35,000 protein band is shown in FIG. 2. A computer search matched this sequence exactly with the sequence of the major histocompatibility antigen HLA-DR.

In order to verify that the procoagulant activity resided with HLA-DR, the protein was isolated using published methods (Read, S. M., et al., Anal. Biochem. 116:53–64 (1981)). HLA-DR was isolated by lentil lectin affinity chromatography followed by immunoaffinity chromatography. The protein that bound to the anti-HLA-DR monoclonal antibody column had strong procoagulant activity with a specific activity of 435 units/mg protein. This activity was about 79-fold higher than that for rabbit thromboplastin under the same conditions. The procoagulant nature of HLA-DR was verified when authentic HLA-DR expressed the same procoagulant activity reported in this work.

Immunochemically isolated HLA-DR enhanced thrombin generation approximately 20-fold in normal plasma during the first four minutes of incubation of the protein in recalcified plasma (FIG. 3a). The final concentration of HLA-DR in the assay was 115 nM. Thrombin generation was enhanced two-fold with 11.5 nM. Since most coagulation factors are present in plasma at micromolar concentrations or greater (Shapiro, S. S., et al., In Hemostasis and Thrombosis (eds. E. J. W. Bowie and A. A. Sharp), Buttersworth, London. pp 197–236 (1985)), HLA-DR appears to be quite efficient in promoting thrombin generation.

The procoagulant activity of HLA-DR was completely inhibited when preincubated with equimolar concentrations of staphylococcal enterotoxin A (SEA). SEA specifically binds to HLA-DR (Fleischer, B., et al., Cell. Immunol. 120:92–101 (1989)). This inhibition served as the basis for qualifying HLA.

EXAMPLE 2

Table 1 shows the procoagulant activity of various cell lines in a coagulation assay with plasma free of fibrinogen. The thrombin generated was tested with S2238 as in Example 1 and the absorbence was increased. The same cell lines were tested with SEA and the results are shown in Table 2. The cell lines are various metastatic cell lines. WM 1158 and WM 373 are melanoma cells.

TABLE 1

Effect of SEA on procoagulant Activity of various melanoma cell lines.

| Procoagulant Activity of Human Melanoma Cells. | |
| --- | --- |
| Cell line Activity | Procoagulant Units/ml Thrombin |
| WM 983.C | 0 |
| WM 983.A | 0 |
| WM 239.A | 9.37 |
| WM 373 | 8.99 |
| WM 1158 | 2.38 |
| WM 1341-D | 1.49 |
| WM 164 | 1.80 |

Of the seven cell lines tested above, only five cell lines had procoagulant activity.

TABLE 2

Effect of Staphylococcal enterotoxin A (SEA) on the procoagulant activity of melanoma cell lines.

| Cell Line | % Reduction of Activity by SEA |
| --- | --- |
| WM 164 | 0 |
| WM 239.A | 0 |
| WM 1341-D | 0 |
| WM 1158 | 34% |
| WM 373 | 42% |

Delineation of the mechanism of thrombin generation by HLA-DR was attempted. The rate of clotting of Factor VII-deficient plasma was enhanced to an extent similar to normal plasma in the presence of HLA-DR (FIG. 3B). HLA-DR's ability to generate thrombin however was dependent on all coagulant factors of the intrinsic pathway. No activity was observed with individual plasmas deficient in factors XII, XI, X, IX, VIII, or V. It is not clear at this time what mechanism(s) is involved in thrombin generation. These results on the coagulation factor requirement have to be viewed with caution, since congenitally deficient plasma known to contain no biological activity may have immunochemically detectable proteins.

The following are illustrative examples.

EXAMPLE 1

There are very few references thus far on the association of bleeding/clotting associated with chemotherapeutic agents. However one very useful one is Edwards, R. L., et al., Heparin Abolishes the Chemotherapy-Induced Increase in Plasma Fibrinopeptide-A Levels. American Journal of Medicine, 89:25–28 (1990).

Tumor cells are grown in culture and treated with various chemotherapeutic agents. The cells are analyzed for increased expression of HLA-DR by the cells. The cells are also tested for increased procoagulant activity. The test shows that HLA-DR procoagulant activity in the tumor cells is inhibited by SEA at a level of 1 to 10 AU per AU of the HLA-DR. The enterotoxin can be used to reduce bleeding and clotting problems in cancer patients in chemotherapy associated with increased HLA-DR.

EXAMPLE 2

Cancer patients with a history of thromboembolic complications are screened and tumor biopsy material tested for the presence/absence of HLA antigens. The level of the HLA antigens is determined. SEA is used to inhibit the HLA-DR antigens in the material as a function of the amount of HLA-DR produced.

EXAMPLE 3

Normal cells of the kidney or liver from two different individuals are co-cultured after tissue typing and screening for increased expression of HLA-DR and associated increase of procoagulant activity in poorly matched cells. The procoagulant activity of the poorly matched cells is tested for the presence of increased HLA-DR. This demonstrates the affect of HLA-DR on graft rejection. The increased activity is then eliminated with SEA to eliminate the mismatch.

EXAMPLE 4

The murine protein corresponding to HLA-DR is called the Ia antigen. Antibodies to the Ia antigen are commercially available. Murine tumor (B16 amelanotic melanoma tumors) previously cultured in vivo in mice have been shown to be composed of at least four subpopulations of similar but non-identical cell types. These cell types are separated into groups by a process of centrifugal elutriation. The cells are separated due to their differing densities and sizes. The four cell types have been classified as Fraction 100, 180, 260 and 340. The 340 fraction contains most procoagulant activity and is the most metastatic. B16 amelanotic melanoma cells metastasize to the lung and form lung colonies following tail vein injections in mice. Lung colonies are allowed to form over twenty-one (21) days for easy staining and visualization. These cell types are isolated and tested to see if the procoagulant activity of these cells, particularly the 340 fraction, is inhibited by the antibody to the Ia antigen.

The cells are incubated with the antibodies to HLA-DR prior to tail vein injections of cells and lung colonies formed are counted.

Staphylococcal enterotoxin A is then used instead of the antibodies to the 1*a* antigen to inhibit the 1*a* antigen. This shows that enterotoxin is effective to inhibit the HLA in metastatic cells and thus reduce metastasis in the mice.

It will be appreciated that the tumor cell HLA's may not be identical to normal HLA-DR. This does not make any difference so long as the endotoxin binds to the HLA.

It is intended that the foregoing description be only illustrative of the present invention and that the present invention be limited only by the hereinafter appended claims.

We claim:

1. A method for measuring a blood procoagulant activity of a human leukocyte antigan comprising:

(a) admixing in vitro an effective amount of *Staphylococcal aureus* enterotoxin A with said human leukocyte antigen in a sample, wherein said human leukocyte antigen is selected from the group consisting of human ovarian carcinoma HLA-DR polypeptides; and (b) measuring an amount of blood coagulation induced in said sample.

2. The method of claim 1 wherein 1 to 10 units enterotoxin A activity is added per unit of said human leukocyte antigen.

3. The method of any one of claims 1 or 2 wherein the blood is blood serum which is free of fibrinogen and is activated with calcium chloride and human leukocyte antigen to generate thrombin.

4. The method of any one of claims 1 or 2 wherein the blood is blood serum which is free of fibrinogen and is activated with calcium chloride and human leukocyte antigen to generate thrombin, wherein the reaction is stopped after a time with EDTA and wherein the thrombin is measured with a thrombin specific chromogenic substrate.

5. The method of any one of claims 1 or 2 wherein the blood is blood serum free of fibrinogen and is activated with calcium chloride and human leukocyte antigen to generate thrombin, wherein the reaction is stopped with EDTA, wherein the thrombin is measured with a thrombin specific chromogenic substrate which is H-D-phenylalanyl-L-pipecoyl-L-arginine-o-nitroanilide dihydrochloride which is stopped after a time with 50% acetic acid.

6. The method of any one of claims 1 or 2 wherein the blood procoagulant activity in the serum is also separately tested with rabbit thromboplastin and the rate of thrombin generation for comparison.

* * * * *